US008420049B2

(12) United States Patent
Abraham

(10) Patent No.: US 8,420,049 B2
(45) Date of Patent: Apr. 16, 2013

(54) LABELED ADENOSINE FOR USE IN POSITRON EMISSION TOMOGRAPHY

(75) Inventor: Edward H. Abraham, Hanover, NH (US)

(73) Assignee: Edward H. Abraham, Hanover, NH (US)

( * ) Notice: Subject to any disclaimer, the term of this patent is extended or adjusted under 35 U.S.C. 154(b) by 0 days.

(21) Appl. No.: 13/399,642

(22) Filed: Feb. 17, 2012

(65) Prior Publication Data

US 2012/0207678 A1    Aug. 16, 2012

Related U.S. Application Data

(60) Division of application No. 10/995,061, filed on Nov. 22, 2004, now abandoned, which is a continuation of application No. PCT/US03/16159, filed on May 22, 2003.

(60) Provisional application No. 60/382,534, filed on May 22, 2002.

(51) Int. Cl.
*A61K 51/00* (2006.01)
*A61M 36/14* (2006.01)

(52) U.S. Cl.
USPC ................................. 424/1.11; 424/1.81

(58) Field of Classification Search .................. 424/1.81
See application file for complete search history.

(56) References Cited

U.S. PATENT DOCUMENTS

| 5,098,996 | A | 3/1992 | Jacobson et al. | |
|---|---|---|---|---|
| 5,811,073 | A | 9/1998 | Kassis et al. | |
| 5,861,503 | A * | 1/1999 | Barrio et al. | 536/27.11 |
| 6,458,355 | B1 * | 10/2002 | Hsei et al. | 424/145.1 |
| 7,148,210 | B2 | 12/2006 | Abraham | |
| 2002/0061279 | A1 * | 5/2002 | DeGrado et al. | 424/1.89 |
| 2005/0244331 | A1 | 11/2005 | Abraham | |

FOREIGN PATENT DOCUMENTS

WO    WO 03/099342 A1    12/2003

OTHER PUBLICATIONS

Nakatsu et al. (Am. J. Physiol. 1972, 223, 1119-1127).*
Baer (Mol. Pharm. 1966, 2, 67-76).*
Shimizu et al. (J. Neurochem. 1972, 19, 687-698).*
Gupta, N.C., et al., "Adenosine in Myocardial Perfusion Imaging Using Positron Emission Tomography," *Am. Heart J.*, 122: 293-301 (1991).
Beanlands, et al., "Heterogeneity of Regional Nitrogen 13-labled Ammonia Tracer Distribution in the Normal Heart: Comparison with Rubidium 82 and Copper 62-labeled PTSM," *J. Nucl. Cardiol.*, 1(3): 225-235 (1994).
Gewirtz, H., et al., "Quantitative PET Measurements of Regional Myocardial Blood Flow: Observations in Humans with Ischemic Heart Disease," *Cardiology*, 88: 62-70 (1997).
Yamamoto, Y., et al., "Noninvasive Quantification of Regional Myocardial Metabolic Rate of Oxygen by $^{15}O_2$ Inhalation and Positron Emission Tomography," *Circulation*, 94(4): 808-816 (1996).
Iskandrian, A.S., et al., "Pharmacologic Stress Testing: Mechanism of Action, Hemodynamic Responses, and Results in Detection of Coronary Artery Disease," *J. Nucl. Cardiol.*, 1(1): 94-111 (1994).
Holschbach, M.H., et al., "$A_1$ Adenosine Receptor Antagonists as Ligands for Positron Emission Tomography (PET) and Single-Photon Emission Tomography (SPET)," *J. Med. Chem.*, 41: 555-563 (1998).
Abraham, E.H., et al., "ATP in the Treatment of Advanced Cancer," Chapter 13 in *Current Topics in Membranes*, vol. 54 (Elsevier Science, USA) (2003).
Krolikiewicz, K., et al., "The Synthesis of 2-Fluoropurine Nucleosides," *Nucleoside & Nucleotides*, 13(1-3): 673-678 (1994).
Abraham, E.H., et al., "Erythrocyte Membrane ATP Binding Cassette (ABC) Proteins: MRP1 and CFTR as Well as CD39 (Ecto-apyrase) Involved in RBC ATP Transport and Elevated Blood Plasma ATP of Cystic Fibrosis," *Blood Cells, Molecules, and Diseases*, 27(1): 165-180 (2001).
Kim, C., et al., "Assessment of Tumor Cell Proliferation Using [$^{18}$F]Fluorodeoxyadenosine and [$^{18}$F]Fluoroethyluracil," *J. Pharm. Sci.*, 85(3): 339-344 (1996).
Baldo, J.H., "2-Fluoro-ATP, a Fluorinated ATP Analog. $^{19}$F Nuclear Magnetic Resonance Studies of the 2-Fluoro-ADP-Myosin Subfragment-1 Complex," *Can J Biochem Cell Biol*, 61(2-3): 115-119 (1983).
Decking, U.K.M., et al., "2-Fluoroadenosine Uptake by Erythroctyes and Endothelial Cells Studied by $^{19}$F-NMR," *Am J Physiol*, 266(4 Pt. 2): H1596-15603 (1994).
Mathews, W.B., et al,, Synthesis and Biodistribution of [$^{11}$C]Adenosine 5'-Monophosphate ([$^{11}$C]AMP), *Mol Imaging Biol*, 7: 203-208 (2005).
Cho, S.Y., et al., "In Vitro Evaluation of Adenosine 5'-Monophosphate as an Imaging Agent of Tumor Metabolism," *J Nucl Med*, 47: 837-845 (2006).
Horti, A.G., et al., "Synthesis of 2-[18F]fluoroadenosine (2-[18F]FAD) as Potential Radiotracer for Studying Malignancies by PET," *Journal of Labelled Compounds and Radiopharmaceuticals*, 49: 811-815 (2006).
Abraham, E.H., et al., "Cystic Fibrosis Hetero- and Homozygosity is Associated with Inhibition of Breast Cancer Growth," *Nat. Med.*, 2: 593 (1996).
Abraham, E.H., et al., "Cystic Fibrosis Transmembrane Conductance Regulator and Adenosine Triphosphate (letter)," *Science*, 275: 1324 (1997).

(Continued)

*Primary Examiner* — Michael G Hartley
*Assistant Examiner* — Melissa Perreira
(74) *Attorney, Agent, or Firm* — Hamilton, Brook, Smith & Reynolds, P.C.

(57) ABSTRACT

Radiolabeled adenosine or radiolabeled adenosine containing molecules for use in positron emission tomography for assessing alterations in adenylate metabolism in a patient are provided.

18 Claims, 4 Drawing Sheets

OTHER PUBLICATIONS

Abraham, E.H., et al., "The Multiple Drug Resistance Protein Functions as an ATP-Channel," *New Engl. Cancer Soc.*, 51: 47 (1990).

Abraham, E.H., et al., "The Multidrug Resistance (mdr1) Gene Product Functions as an ATP Channel," *Proc. Natl. Acad. Sci.*, 90: 312 (1993).

Ucsugi, S., et al., "Synthesis and Properties of ApU Analogues Containing 2'-Halo-2'-deoxyadenosines. Effects of 2' Substituents on Oligonucleotide Conformation," *Biochemistry*, 21: 5870-5877 (1982).

Malspeis, L., et al., "Pharmacokinetics of 2-F-ara-A (9-β-D-Arabinofuranosyl-2-fluoroadenine) in Cancer Patients During the Phase I Clinical Investigation of Fludarabine Phosphate," *Semin. Oncol.*, 17(5): 18-32 (1990).

Alauddin, M.M., et al., Synthesis of [$^{18}$F]-Labeled Adenosine Analogs as Potential PET Imaging Agents, *J. Label Compd Radiopharm*, 46: 805-814 (2003).

Mathews, W.B., et al., "[$^{11}$C] 5'-adenosine adenosine Monophosphate ([$^{11}$C] AMP): A New Radioligand for Positron Emission Tomographic Imaging of Cancer," *J Nucl Med*, 43: 362P (Abstract) (2002).

Sterling, Jr., K.M., et al., "Cystic Fibrosis Transmembrane Conductance Regulator in Human and Mouse Red Blood Cell Membranes and its Interaction with Ecto-Apyrase," *Journal of Cellular Biochemistry*, 91: 1174-1182 (2004).

Abraham, E.H., et al., "Cellular and Biophysical Evidence for Interactions Between Adenosine Triphosphate and P-Glycoprotein Substrates: Functional Implications for Adenosine Triphosphate/Drug Cotransport in P-Glycoprotein Overexpressing Tumor Cells and in P-Glycoprotein Low-Level Expressing Erythrocytes," *Blood Cells, Molecules, and Diseases*, 27(1): 181-200 (2001).

Kubota, K. et al., "Differential Diagnosis of AH109A Tumor and Inflammation by Radioscintigraphy with L-[Methyl-$^{11}$C]methionine," *Jpn. J. Cancer Res.*, 80: 778-782 (1989).

International Search Report for Int'l Application No. PCT/US03/16159; Date Mailed: Aug. 22, 2003.

Meyer, R.B., et al., A Convenient Synthesis of Carbon Labeled Adenine Nucleotides: Adenonsine-2-$^{13}$C 5'—Phosphate, *J. Label. Comp. and Radiopharm.*, 18: 1119-1122 (1980).

Moyer, J.D., et al., "Nucleoside Triphosphate Specificity of Luciferase", *Analytical Biochem.*, 131: 187-189 (1983).

Office Action, U.S. Appl. No. 10/995,061, Mail Date: May 21, 2007.

Final Office Action, U.S. Appl. No. 10/995,061, Mail Date: Nov. 29, 2007.

Office Action, U.S. Appl. No. 10/995,061, Mail Date: Aug. 11, 2008.

Final Office Action, U.S. Appl. No. 10/995,061, Mail Date: Feb. 10, 2009.

Office Action, U.S. Appl. No. 10/995,061, Mail Date: Feb. 24, 2010.

Appeal Brief, U.S. Appl. No. 10/995,061, Dated: Oct. 20, 2010.

Examiner's Answer, U.S. Appl. No. 10/995,061, Mail Date: Jan. 18, 2011.

Decision on Appeal, U.S. Appl. No. 10/995,061, Mail Date: Dec. 21, 2011.

Abraham, E., et al., "ATP in the Treatment of Advanced Cancer", *Current Topics in Membranes*, vol. 54, pp. 415-452 (2003).

Knowles, M.R., "Pharmacologic Treatment of Abnormal Ion Transport in the Airway Epithelium in Cystic Fibrosis," *Chest*, 107(2):71S-76S, (1995).

Lehninger, Biochemistry, second edition, Chapter 15 pp. 387-416 (1975).

\* cited by examiner

*In vitro* metabolism of [$^{11}$C] AMP in whole human blood

*In vitro* metabolism of [$^{11}$C] AMP in whole human blood treated with 500 μM dipyridamole Effect of dipyridamole treatment on *in vivo* blood uptake of [11C] AMP Effect of dipyridamole treatment on *in vivo* lung uptake of [$^{11}$C] AMP

LABELED ADENOSINE FOR USE IN POSITRON EMISSION TOMOGRAPHY

RELATED APPLICATION

This application is a divisional of U.S. application Ser. No. 10/995,061, filed on Nov. 22, 2004 now abandoned, which is a continuation of International Application No. PCT/US03/16159, which designated the United States and was filed on May 22, 2003, published in English, which claims the benefit of U.S. Provisional Application No. 60/382,534, filed May 22, 2002. The entire teachings of the above applications are incorporated herein by reference.

BACKGROUND OF THE INVENTION

Positron emission tomography (PET) is a non-invasive technique that allows serial metabolic measurements to be obtained in a single subject. PET imaging is particularly useful in assessing myocardial viability via the ability of this technique to demonstrate metabolic consequences of myocardial ischemia. Using PET imaging, myocardial segments that are likely to improve after revascularization can be identified. Further, this technique can be used in the detection of coronary artery disease and serves as an alternative test for patients who cannot undergo treadmill exercise stress testing.

Adenosine is administered routinely as a pharmacologic stress agent to assess cardiac disease by positron emission tomography. For this assessment, a separate radiolabeled tracer is also administered to the patient. Adenosine is preferred as a vasodilator over dipyramidole as it produces maximum vasodilation in a significantly greater percentage of patients and is a more potent coronary vasodilator (Gupta et al. Am. Heart J. 122:293-301 (1991)). Further, adenosine's short half-life is ideal for use with the very short half-life radiotracers used for PET.

A number of radiotracers or imaging agents have been described for use in PET in conjunction with adenosine. Some examples include $^{13}$N-ammonia (Beanlands et al. *J. Nucl. Cardiol.* 1(3):225-35 (1994); Gewirtz et al. *Cardiology,* 88(1):62-70 (1997)), 2-[$^{18}$F]fluoro-2-deoxy-D-glucose (McFalls et al. 272:343-9 (1997)), and $^{15}$O$_2$ (Yamamoto et al. *Circulation,* 94(4):808-16 (1996)). Thallium-201- and technetium-labeled perfusion agents are also used in accessing myocardial perfusion (Iskandrian et al. *J. Nucl. Cardiol.,* 1(1):94-111 (1994)). In addition, $^{11}$C methyl triphenyl phosphonium has been disclosed as a promising PET agent for cardiac imaging. The high affinity of 8-cyclopentyl-1,3-dipropylxanthine (CPX) for the A1 adenosine receptor has also been suggested to provide good leads for developing radioligands suitable for PET (Holsbach et al., *J. Med. Chem.,* 41(4):555-63 (1998)).

Radiofluorinated ethyluracil and deoxyadenosine analogues have also been used in the noninvasive assessment of tumor proliferation by PET (Kim et al., *J. Pharm. Sci.,* 85(3): 339-44 (1996)).

Attempts have been made to study adenylate metabolism but these methods are limited to rapid hydrolysis that occurs with rapid loss of label. Additionally, existing methods for biological imaging have limitations including undesirable sensitivities and decreased specificity of existing imaging agents. Other problems include inability to cross the blood brain barrier and difficulties with localization. Therefore, a need exists for developing new PET imaging agents with improved properties.

SUMMARY OF THE INVENTION

It has now been found that adenylate metabolism can be assessed by positron emission tomography (PET) using a PET imaging agent comprising radiolabeled adenosine or a radiolabeled adenosine containing molecule such as ATP, ADP or AMP or the corresponding 2-deoxyribose analog. Abnormal adenosine and ATP transport is associated with genetic diseases including, but not limited to, cystic fibrosis, diabetes, cancer and cardiac disease. Accordingly, the present invention relates to PET imaging agents comprising radiolabeled adenine or a radiolabeled adenine containing molecules such as ATP, ADP or AMP or the corresponding 2-deoxyribose analogs. In certain embodiments, the adenine or adenine containing molecule is labeled with $^{11}$C, $^{13}$NH$_2$ or $^{18}$F.

The invention further provides methods of assessing alterations in adenylate metabolism in a patient comprising administering to the patient radiolabeled adenine or a radiolabeled adenine containing molecule and tracing the radiolabeled adenine or radiolabeled adenine containing molecule by positron emission tomography so that alterations in adenylate metabolism in the patient can be assessed.

DETAILED DESCRIPTION OF THE INVENTION

Figure 1:
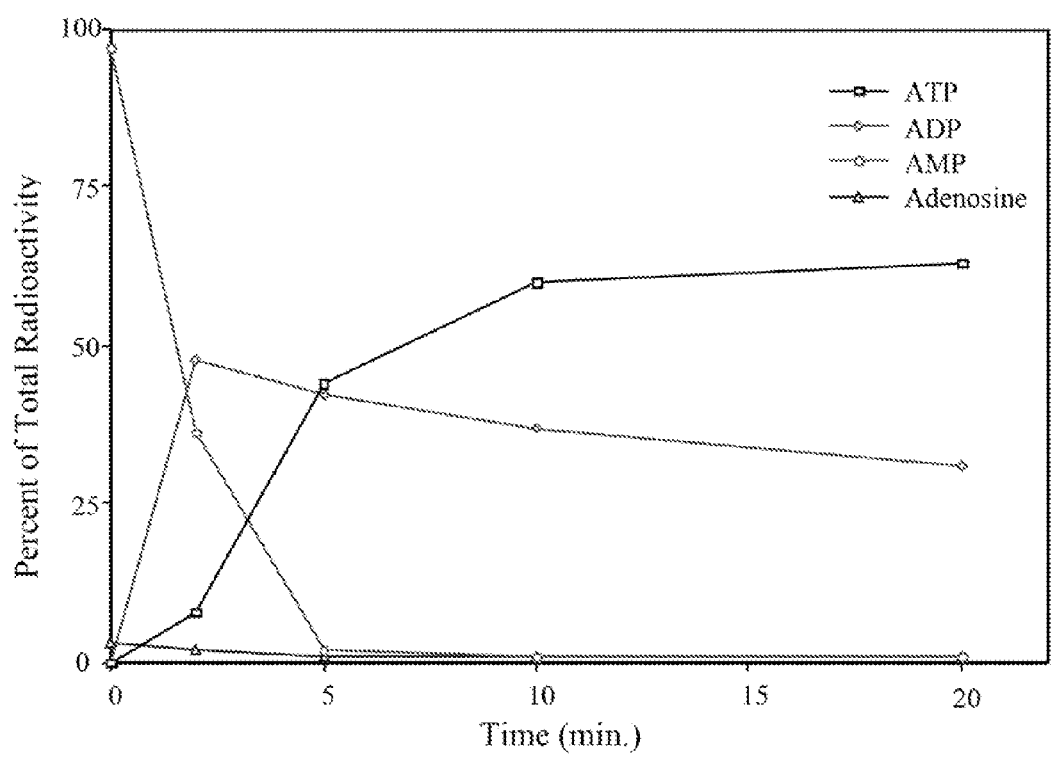
FIG. 1 is a graph depicting the In vitro metabolism of [11C] AMP in whole human blood.

A description of preferred embodiments of the invention follows.

The present invention is directed to the use of radiolabeled adenine or a molecule containing an adenine group such as ATP, ADP or AMP or the corresponding 2-deoxyribose analogs in assessing alterations in adenylate metabolism via positron emission tomography in patients suffering from genetic diseases including, but not limited to, cystic fibrosis, diabetes, cancer and cardiac disease. The radiolabel is preferably a positron emitter. Labeled adenine agents can be administered to a patient to image adenosine metabolism, transport and localization. Adenylate imaging can be used for assessing new therapies targeting purine receptors. An advantage of labeling adenine groups for tumor imaging is due to the low uptake of adenosine in the brain but a high tumor uptake of adenosine increasing sensitivity of the method. Also, an advantage exists for imaging due to the availability of adenine groups on red blood cells which circulate throughout the body. Also radiolabeled ATP is more robust due to trapping of the adenylate from phosphorylation one the molecule is across the cell membrane. The radiolabeled ATP of the invention is less able to get out of the cell which also results in increased sensitivity.

For patients suffering from cystic fibrosis and diabetes, this imaging is useful in diagnosing individuals with more severe forms of these diseases and for monitoring response to therapy. For patients suffering from cancer, imaging of radiolabeled adenosine is useful in localizing tumors and metastases, designing new therapeutics and monitoring response to treatment. For patients suffering from cardiac disease, labeled adenosine offers a new dimension in disease assessment.

The radiolabel is preferably a positron-emitting isotope. In certain embodiments, the adenine or adenine containing molecule is labeled with $^{11}$C, $^{13}$NH$_2$, $^{76}$Br, $^{144}$I or $^{18}$F. The radio-label can additionally be chosen by desired half-life for the chosen indication.

In one embodiment, the present invention is $^{11}$C labeled adenine, $^{11}$C-labeled adenosine or a compound comprising an $^{11}$C labeled adenine or adenosine. Examples of such molecules include AMP, ADP, ATP or the corresponding 2-deoxyribose analogs. In certain embodiments, the $^{11}$C labeled adenine or adenosine is 2-$^{11}$C-adenine or 2-$^{11}$C-adenosine. For molecules comprising $^{11}$C adenine, the $^{11}$C is typically at the C-2 position, but can be located at any carbon position on the molecule including the sugar moiety.

In molecules comprising an $^{11}$C labeled adenine, the $^{11}$C-labeled adenine is typically connected to the remainder of the molecule by a covalent bond at the seven nitrogen, and in molecules comprising an $^{11}$C labeled adenosine, the $^{11}$C-labeled adenosine is typically connected to the remainder of the molecule by a covalent bond at the 3'-hydroxyl and/or 5'-hydroxyl.

Yet another embodiment of the present invention is a method of using an $^{11}$C-adenine molecule containing or $^{11}$C-adenosine-containing molecule for PET imaging in a patient, e.g., to assess alterations in adenylate metabolism in patients via PET. [$^{11}$C] Adenosine 5'-monophosphate is synthesized as described below and in the Exemplification.

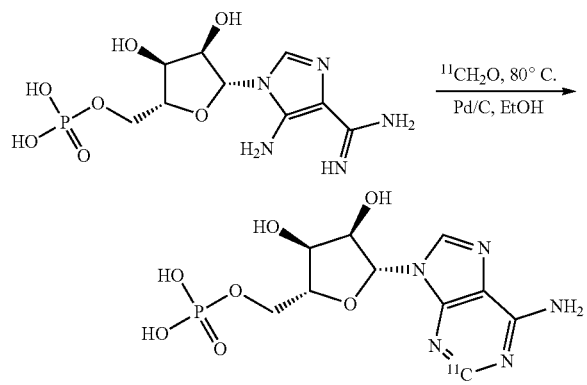

Another embodiment of the present invention is $^{18}$F labeled adenine, $^{18}$F-labeled adenosine or a compound comprising an $^{18}$F labeled adenine group or adenosine group. Examples of such molecules include AMP, ADP, ATP or the corresponding 2-deoxyribose analogs. In certain embodiments, the $^{18}$F labeled adenine or adenosine is 2-$^{18}$F-adenine or 2-$^{18}$F-adenosine. In yet other embodiments, the $^{18}$F labeled adenine or adenosine is 8-$^{18}$F-adenine or 8-$^{18}$F-adenosine.

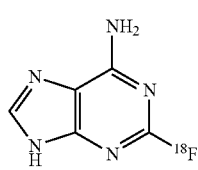

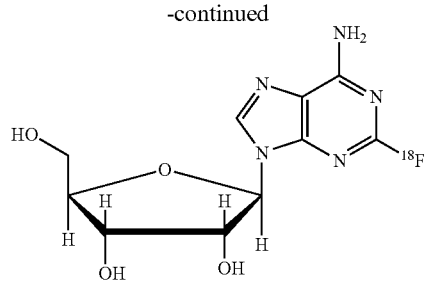

In molecules comprising an $^{18}$F labeled adenine, the $^{18}$F-labeled adenine is typically connected to the remainder of the molecule by a covalent bond at the seven nitrogen, and in molecules comprising an $^{18}$F labeled adenosine, the $^{18}$F-labeled adenosine is typically connected to the remainder of the molecule by a covalent bond at the 3'-hydroxyl and/or 5'-hydroxyl.

Yet another embodiment of the present invention is a method of using an $^{18}$F-adenine molecule containing or $^{18}$F-adenosine-containing molecule for PET imaging in a patient, e.g., to assess alterations in adenylate metabolism in patients via PET.

Methods for radiolabeling adenine nucleotides with labels such as $^{13}$C have been described by Meyer and Wong (*J. of Labelled Compounds and Radiopharmaceuticals*, 18(8) 1119-1122 (1981)). Methods have also been described for synthesis of $^{15}$NH$_2$-adenosine. Such methods can be routinely adapted by those of skill in the art to produce radiolabeled adenosine or an adenosine containing molecule with a radiolabel such as $^{11}$C, $^{18}$F or $^{13}$NH$_2$ for use in PET.

Methods for preparing 2-F-adenosine are described in Krolikiewicz and Vorbruggen, Nucleoside & Nucleotides 13(1-3), 673-678 (1994), the entire teaching of which are incorporated herein by reference. The synthesis is shown schematically below:

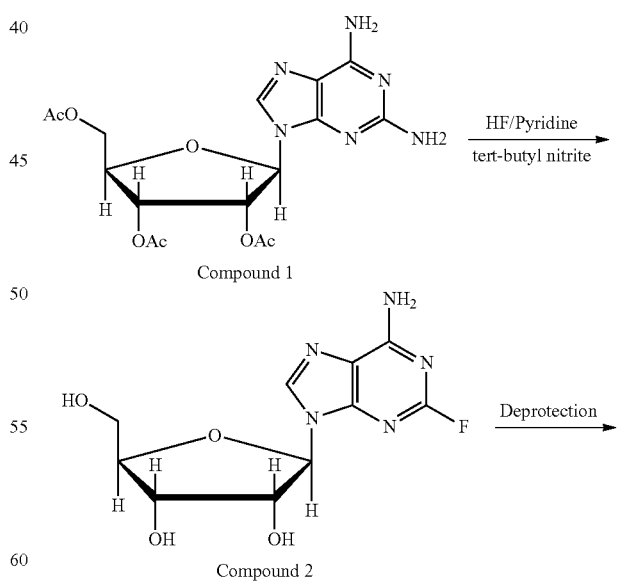

Briefly, Compound 1 is reacted with H$^{18}$F/pyridine and tert-butyl nitrite to form 2',3',5'-tri-O-acetyl-2-$^{18}$F-adenosine. Deprotection yields 2-$^{18}$F-adenosine.

The quantity of the imaging agent used, the route by which it is administered and the formulation will be selected so that the imaging agent will reach the target, i.e., the site being imaged. Most commonly, the agent is administered intravenously. As such, the formulation will typically be suitable for injection. Standard pharmaceutical formulation techniques can be employed, such as those described in Remington's Pharmaceutical Sciences, Mack Publishing Company, Easton, Pa. Suitable pharmaceutical carriers for intravenous administration include, for example, sterile water, physiological saline, bacteriostatic saline (saline containing about 0.9% mg/ml benzyl alcohol), phosphate-buffered saline, Hank's solution, Ringer's-lactate and the like. Oral administration is also commonly used. For oral administration, the imaging agent can be combined with a suitable solid or liquid carrier or diluent to form capsules, tablets, pills, powders, syrups, solutions, suspensions and the like.

The tablets, pills, capsules, and the like contain from about 1 to about 99 weight percent of the imaging agent and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

After administration of the radiolabeled adenine or adenosine-containing compound, the biodistribution of the radiolabeled compound is assessed by positron emission tomography according to methods known in the art.

Upon injection, adenosine is rapidly converted to ATP in the liver and transported to multiple sites throughout the body. Accordingly, upon injection of radiolabeled adenosine or a radiolabeled adenosine containing molecule, labeled adenylates are transported from the liver to tumors, and organ sites including the brain thus enabling detection of unique imaging patterns by positron emission tomography in a patient. Unique imaging patterns can be observed for various disease states wherein adenosine and ATP transport are abnormal. Examples of such diseases states include, but are not limited to, cystic fibrosis, diabetes, cancer and cardiac disease. The ability to perform these scans permits detailed assessment of alterations in adenylate metabolism. Further, with respect to cancer, PET imaging with radiolabeled adenosine or adenosine containing molecules permits localization of tumor micrometastases and assists in identifying appropriate therapeutic approaches for the disease.

Transmembrane ATP transport has been observed to be associated with the presence of cystic fibrosis transmembrane conductance regulator (CFTR), P-glycoprotein (Pgp, also known as the multidrug resistance protein, MDR), Multidrug Resistance-associate Protein (MRPI) and other proteins in a variety of nucleated mammalian cells. Collectively these proteins involved with transmembrane ATP transport belong to the superfamily of ATP binding cassette (ABC) membrane proteins. Abnormal levels of ATP in blood plasma and RBCs were observed with diminished levels of ATP along epithelial surfaces of cystic fibrosis subjects (e.g., along airway and gastrointestinal tract apical surfaces) CFTR functions as an ATP channel. Heterozygous and homozygous CFTR mice had elevated ATP levels. Experiments were conducted with [$^{14}$C]-ATP in gene knockout mice as described in Blood Cells, Molecules, and Diseases, 27(1):164-180 (2001) by Abraham et al. The in vivo implications and association of ABC proteins with ATP transport were studied in CFTR knockout mice. Briefly, two hours after administration of the labeled ATP, animals were sacrificed. Homogenates of various organs were and radioactivity of the homogenates was measured in a scintillation counter. The biodistribution compared to controls was determined.

Table 1 provides results from these experiments.

TABLE 1

[$^{14}$C]-ATP Biodistribution Ratios in ABC knockout/wild-type ratios.

| Mouse genoype | CFTR | CD39 (−/−)/ CD39 (+/+) | MRP | CD39 (−/−)/ CD39 (+/+) |
|---|---|---|---|---|
| Blood | 24.2 | 1.9 | 0.72 | 0.17 |
| Liver | 1.4 | 0.55 | 0.66 | 0.65 |
| Intestines | 0.58 | 0.89 | 0.58 | 0.96 |
| Kidney | 1.1 | 0.75 | 0.88 | 0.62 |
| Lung | 0.82 | 0.15 | 1.7 | 0.52 |
| Heart | 0.81 | 0.71 | 0.83 | 0.81 |
| Brain | 1.4 | 0.88 | 1.6 | 0.19 |

As can be seen from the results in Table 1, differences compared to control animals in biodistribution of adenylate were observed for all gene knockout mice studied including the model for cystic fibrosis (CFTR), tumor related gene knockouts (MDR and MRP) and CD39. Notably, CFTR knockout mouse [$^{14}$C] purine ratio had significant elevation, whereas MRP and CD39 had decreased ratios. In CRTR knockout mice, intestinal and airway [$^{14}$C] purine ratios were decreased. This reduction is consistent with diminished purine accumulation in these respective organs Using adenosine or an adenosine containing molecule labeled with a radionuclide detectable by PET such as $^{11}$C 18F or $^{13}$NH$_2$, these differences in the biodistribution of adenylate in various disease states can be detected by PET.

For example, in patients with cancer there is abnormal adenosine and ATP transport and metabolism at the tumor site. The ability to image adenylate uptake and distribution in tumors is therefore useful in localizing tumors and metastases. Further monitoring adenylate uptake by tumors which is indicative of a response to treatment can be useful in designing new radiation and chemotherapies.

In addition, elevation of blood ATP has recently been associated with the pathogenesis of cystic fibrosis. However, not all genetic abnormalities classified as cystic fibrosis have the same disease severity. Thus, by imaging with radiolabeled adenosine or a radiolabeled adenosine containing molecule, patients with more severe forms of the disease can be distinguished. Further, response to new therapies for cystic fibrosis can be monitored. A positive response to therapy would be a decrease of blood ATP from an elevated state. The pattern of adenylate metabolism in a treated patient would be compared to a pattern determined in healthy individuals. Elucidation of these differences could be exploited for improved therapies. Aspects of adenosine and ATP transport are also abnormal in diabetic patients. Elevated ATP levels are associated with diabetic patients. Accordingly the radiolabeled adenosine PET imaging agents of the present invention can also be used in assessing disease severity in diabetic patients and in monitoring responses to therapies. A positive response to therapy would be a reduction in ATP levels.

Further, the availability of radiolabeled adenosine and the ability to image its metabolism, transport and localization in patients offers a new dimension in the assessment of individuals with cardiac disease via PET.

The following nonlimiting examples are provided to further illustrate the present invention.

EXAMPLES

Example 1

The Synthesis and Biodistribution of [$^{11}$C] Adenosine 5'-Monophosphate ([$^{11}$C] AMP)

Materials and Methods
General.
All chemicals and solvents were ACS or high performance liquid chromatography (HPLC) purity and were used as received. The 5-amino-1-β-D-ribofuranosylimidazole-4-carboxamidine-5'-phosphate precursor was synthesized by R.I. Chemical, Inc. of Orange, Calif. following a literature procedure [5]. [$^{11}$C] Formaldehyde was prepared by lithium aluminum hydride reduction of [$^{11}$C]carbon dioxide carried out at −10° C. [7]. The HPLC system consisted of two Waters model 590EF pumps, two Rheodyne model 7126 injectors, Alltech $C_{18}$ Econosil columns, an in-line Waters model 440 ultraviolet detector (254 nm), and a single sodium iodide crystal flow radioactivity detector. All HPLC chromatograms were recorded by a Rainin Dynamax dual channel control/interface module connected to a Macintosh computer running Dynamax version 1.4 program software. Radioactivity measurements were made using a Capintec CRC-15R dose calibrator.

Synthesis of [$^{11}$C] Adenosine 5'-Monophosphate ([$^{11}$C] AMP)

Figure 2:
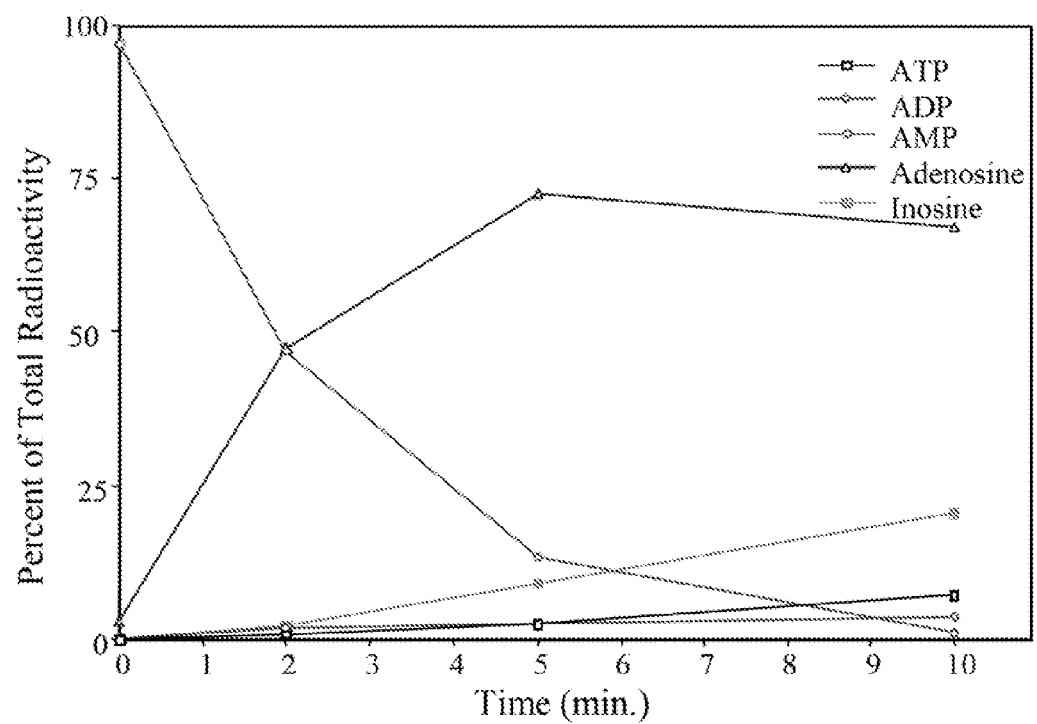
FIG. 2 is a graph depicting the In vitro metabolism of [$^{11}$C] AMP in whole human blood treated with 500 μM dipyridamole.

[$^{11}$C] Carbon dioxide was bubbled into 600 μL of a 0.1M solution of lithium aluminum hydroxide in THF at −10° C. The reaction was quenched by adding 500 μL of 2M sulfuric acid, and the cold bath was removed. The [$^{11}$C] formaldehyde was transferred by an argon stream and heating to a second vial containing 1 mg of 5-amino-1-β-D-ribofuranosylimidazole-4-carboxamidine-5'-phosphate and 0.5 mg of 10% Pd/C in 100 μL of ethanol which was cooled to 0° C. Once the radioactivity reached a plateau, the vial was removed from the ice bath, and 40 μL of 6M sodium hydroxide was added. The reaction mixture was heated at 80° C. for 10 minutes. After heating, the reaction mixture was filtered, and the filter was rinsed with 200 μL of 1M hydrochloric acid. The filtrate was reduced in volume under a stream of argon and neutralized with 250 μL of 8.4% sodium bicarbonate. The solution was diluted with 1 mL of water containing 0.15% acetic acid and injected onto a C8 HydroBond AQ semi-preparative HPLC column. The column was eluted with 100% water containing 0.15% acetic acid at a flow rate of 6 mL/min. The radioactive peak corresponding to [$^{11}$C] AMP ($t_R$=6.2 min, see FIG. 2) was collected in a rotary evaporator modified for remote addition and removal of solutions. The HPLC solvent was evaporated at 80° C. under reduced pressure in the presence of 4 mL of ethanol. After evaporation, the residue was dissolved in 7 mL of saline and sterile filtered into a pyrogen-free bottle. The solution was then diluted with 3 mL of 8.4% sodium bicarbonate solution.

A 100 μL aliquot of the final product was injected onto a C8 HydroBond AQ analytical HPLC column and eluted with 100% water containing 0.15% acetic acid at a flow rate of 3 mL/min. The radioactive peak corresponding to [$^{11}$C] AMP ($t_R$=3.6 min) coeluted with a standard sample. Chemical purity, radiochemical purity, and specific activity were all determined by analytical HPLC. Specific activity was calculated by relating the area of the UV absorbance peak of carrier ligand in an aliquot of known radioactivity to the area of a standard sample.

In Vitro Metabolism of [$^{11}$C] AMP.

Human plasma was prepared from heparinized blood of a healthy volunteer. 50 μL of [$^{11}$C] AMP (39.96-70.82 GBq/μmol, 1080-1914 mCi/μmol) was added to 1 mL of plasma or heparinized whole blood at 37° C. In one series of studies, dipyridamole was added to give a concentration of 500 μM in whole blood. One hundred μL samples, which were removed from the incubation mixture at 0, 2, 5, 10, 20, and 30 minutes, were added to 350 μL of water at 0° C. and acidified with 50 μL of 5N perchloric acid. After standing for 5 minutes on ice, the protein precipitate was removed by centrifugation at 13,000×g for 1 minute in a microcentrifuge. The acid soluble supernatant was analyzed by HPLC. Chromatographic separation of the labeled adenosine phosphate esters used a Phenomenex Synergi Polar RP column (4.6×250 mm, 10 micron particle size) eluted with 0.1N perchloric acid at 2 mL/min. Radioactivity was detected by a dual BGO flow detector (Bioscan Inc., Washington D.C.). Optical detection was at 254 nm. Data from both detectors was collected and analyzed by Laura software (Bioscan Inc., Washington D.C.).

Ex Vivo Distribution of [$^{11}$C] AMP in Mice.

Non-fasted, male CD-1 mice (25 g) were injected via the tail vein with 15.5 MBq (418 μCi, 2.57 μg/kg) of [$^{11}$C] AMP. Three mice each were sacrificed by cervical dislocation at 5, 30, and 60 minutes after injection. The lungs, heart, kidneys, liver, spleen, intestine, stomach, and brain were quickly removed and put on ice. One femur and samples of thigh muscle and blood were also collected. The organs were weighed, and the tissue radioactivity measured with an automated gamma counter (LKB Wallac 1282 Compugamma CS Universal Gamma Counter). The percent injected dose per gram of tissue (% ID/g) was calculated by comparison with samples of a standard dilution of the initial dose. All measurements were corrected for decay.

Effect of Dipyridamole Treatment in Mice.

The effect of dipyridamole treatment on the uptake and distribution of [$^{11}$C] AMP, nine mice were given a 30 mg/kg dose of dipyridamole ip 60 minutes prior to administration of the radiotracer was determined. Three mice each were sacrificed 5, 30, and 60 minutes after injection of 23.8 MBq (642 μCi, 8.7 μg/kg) of [$^{11}$C] AMP. All tissue samples were handled as described above.

[$^{11}$C] AMP Dosimetry in Mice.

All animal studies were carried out in full compliance with government and institutional guidelines relating to the conduct of animal experiments. After tying off the urethral meatus, normal, non-fasted, male CD-1 mice (25 g) were injected via the tail vein with 8.33 MBq (225 μCi, 1.0 μg/kg) of [$^{11}$C] AMP. Three mice each were sacrificed by cervical dislocation at 5, 15, 30, 45, 60, and 90 minutes after injection. The kidneys, bladder, heart, small intestine, spleen, liver, stomach, lungs, testes, large intestine, and brain were quickly removed and put on ice. The femur was dissected to remove marrow. Samples of thigh muscle and blood were also collected. The organs were weighed, and the tissue radioactivity measured with an automated gamma counter (LKB Wallac 1282 Compugamma CS Universal Gamma Counter). The radiation dose burden to each organ was calculated by the MIRD method. All measurements were corrected for decay.

Results
Radiochemistry

The average time for radiosynthesis, HPLC purification, and formulation was 34 minutes from end-of-bombardment. The radiochemical yield was 2.4% based on [$^{11}$C] formaldehyde. At end-of-synthesis, an average (n=7) 603 MBq (16.3 mCi) of [$^{11}$C] AMP was isolated with a specific activity of 90.10 GBq/µmmol (2435 mCi/µmol). The final formulation was >98% radiochemically pure as determined by analytical HPLC.

In Vitro Metabolism of [$^{11}$C] AMP

Figure 3:
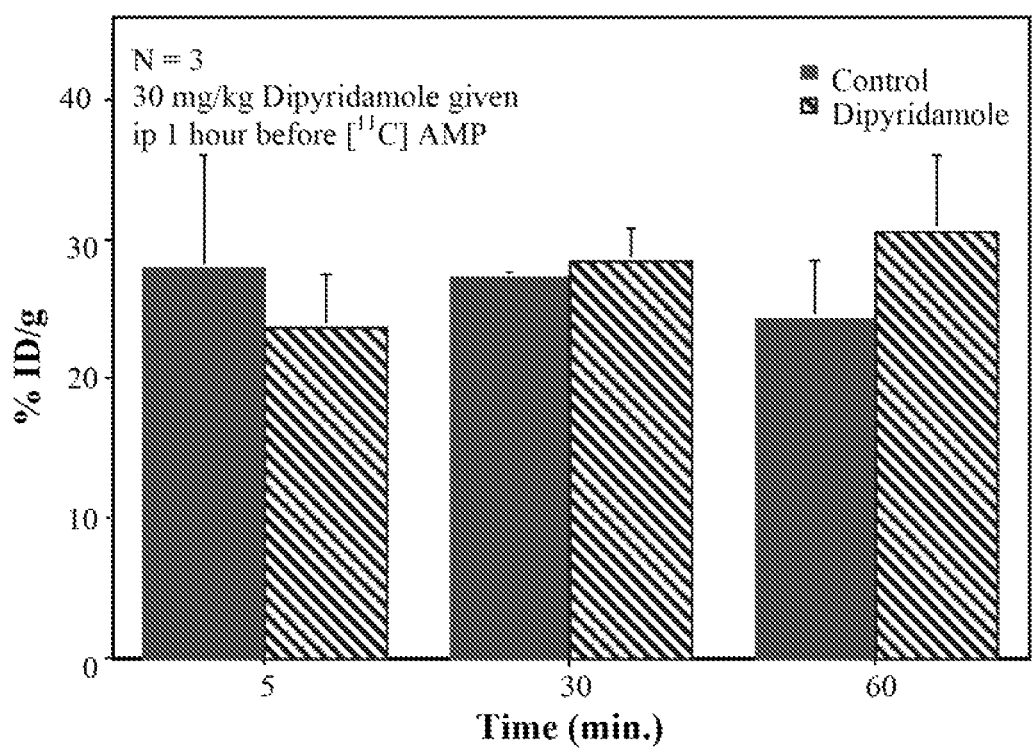
FIG. 3. is a graph depicting the effect of dipyridamole treatment on in vivo blood uptake of [$^{11}$C] AMP.
Figure 4:
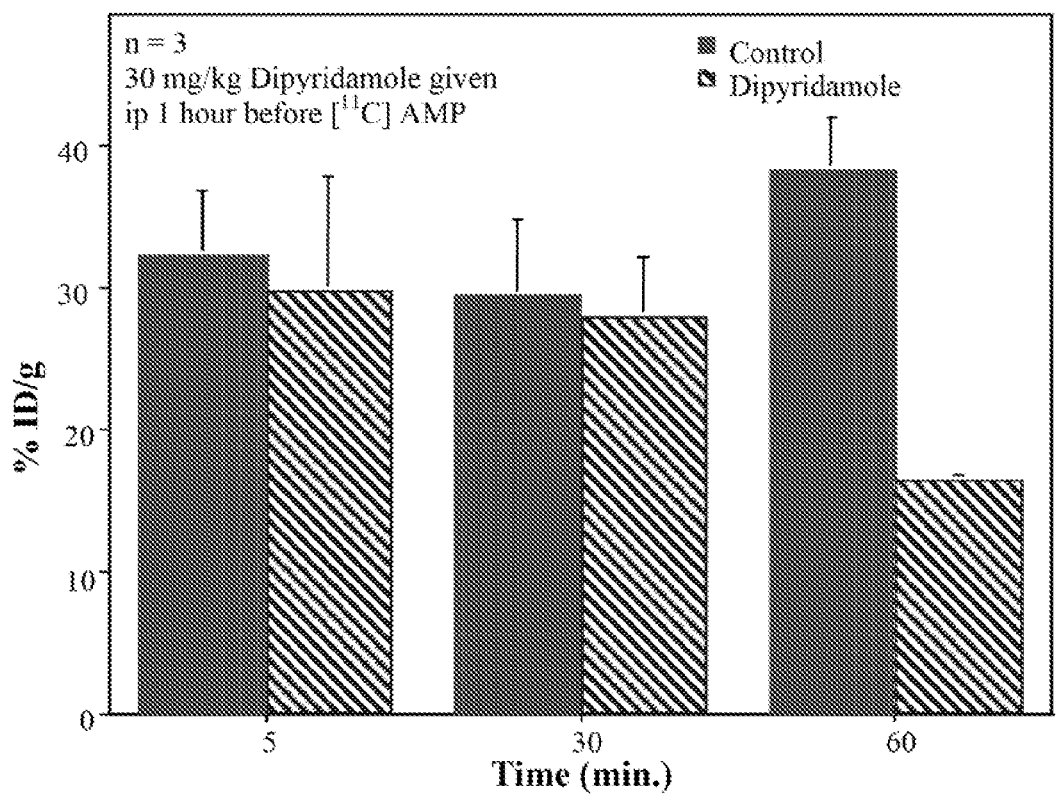
FIG. 4 is a graph depicting the effect of dipyridamole treatment on in vivo lung uptake of [$^{11}$C] AMP.

The HPLC retention times for the four adenylate species observed were: ATP (1.95 min), ADP (2.20 min), AMP (3.35 min) and adenosine (5.30 min). FIG. 3 shows that metabolic analysis of [$^{11}$C] AMP in whole human blood indicated >60% conversion to ATP after 10 minutes. FIG. 4, however, shows that dipyridamole treated whole blood converted >60% of the tracer to adenosine after only 5 minutes. Treatment of isolated human plasma with [$^{11}$C] AMP showed similar results to dipyridamole treated whole blood. See FIG. 1 and FIG. 2.

Ex Vivo Distribution of [$^{11}$C] AMP in Mice

The distribution of [$^{11}$C] AMP in live mice was determined for most major organs after intravenous injection of the tracer. Table 2 shows the decay-corrected % ID/g data for these organs at 5, 30, and 60 minutes post-injection.

TABLE 2

Ex vivo mouse biodistribution data for [$^{11}$C] AMP (% ID/g)

| Organ | 5 Minutes | 30 minutes | 60 minutes |
|---|---|---|---|
| Lungs | 32.37 ± 4.52 | 29.52 ± 5.42 | 38.48 ± 3.63 |
| Blood | 27.94 ± 8.21 | 27.34 ± 0.41 | 24.34 ± 4.13 |
| Heart | 20.09 ± 3.24 | 18.07 ± 5.19 | 20.47 ± 2.87 |
| Kidneys | 8.88 ± 3.82 | 9.31 ± 2.88 | 6.80 ± 4.10 |
| Liver | 7.56 ± 3.98 | 2.99 ± 0.10 | 3.53 ± 0.55 |
| Spleen | 2.96 ± 1.49 | 4.75 ± 0.67 | 4.71 ± 1.06 |
| Muscle | 2.14 ± 0.61 | 3.67 ± 0.54 | 3.63 ± 1.04 |
| Bone | 2.35 ± 0.68 | 2.57 ± 0.34 | 3.21 ± 0.48 |
| Intestine | 1.74 ± 0.41 | 1.80 ± 0.50 | 2.17 ± 1.06 |
| Stomach | 1.98 ± 0.36 | 1.12 ± 0.25 | 2.10 ± 0.98 |
| Brain | 0.78 ± 0.18 | 1.06 ± 0.19 | 0.80 ± 0.26 |

Data are means ± SD (n = 3)

Effect of Dipyridamole Treatment in Mice

As shown in FIG. 3 and FIG. 4, treating the mice with 30 mg/kg of dipyridamole [10] significantly decreased the uptake of [$^{11}$C] radiotracer in the lungs at 60 minutes but did not affect the amount of tracer in the blood.

[$^{11}$C] AMP Dosimetry in Mice

The radiation dose burden to each organ of a mouse was calculated by the MIRD method. As shown in Table 3, the critical organs for radiation dose burden were the kidneys, followed by bladder, heart, small intestine, spleen, and liver.

TABLE 3

Mouse dosimetry data for [$^{11}$C] AMP

| Organ | mGy/MBq | rad/mCi |
|---|---|---|
| Kidneys | 2.34E−2 | 8.66E−2 |
| Bladder | 1.77E−2 | 6.56E−2 |
| Heart | 8.99E−3 | 3.33E−2 |
| Upper GI | 8.97E−3 | 3.32E−2 |
| Spleen | 7.54E−3 | 2.79E−2 |
| Liver | 6.45E−3 | 2.39E−2 |
| Stomach | 6.36E−3 | 2.35E−2 |
| Lungs | 5.66E−3 | 2.10E−2 |
| Lower GI | 5.52E−3 | 2.04E−2 |
| Testes | 5.37E−3 | 1.99E−2 |
| Red Marrow | 3.88E−3 | 1.44E−2 |
| Bone Surface | 3.11E−3 | 1.15E−2 |
| Muscle | 2.89E−3 | 1.07E−2 |
| Carcass | 2.82E−3 | 1.04E−2 |
| Brain | 1.87E−3 | 6.91E−3 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of assessing alterations in adenylate metabolism in a patient having a disease with abnormal adenosine and ATP transport and metabolism, wherein the method comprises administering to the patient radiolabeled oxygenated adenine or a radiolabeled oxygenated adenine containing molecule, wherein the oxygenated adenine or oxygenated adenine containing molecule is radiolabeled on the adenine group with $^{11}$C, $^{18}$F or $^{13}$NH$_2$, and tracing biodistribution of the radiolabeled oxygenated adenine or radiolabeled oxygenated adenine containing molecule by positron emission tomography for assessing alterations in adenylate metabolism in the patient.

2. The method of claim 1, wherein the adenine or adenine containing molecule comprises an $^{18}$F-labeled adenine group.

3. The method of claim 2, wherein the adenine or adenine containing molecule comprises a 2-$^{18}$F-labeled adenine group.

4. The method of claim 3, wherein the $^{18}$F-labeled adenine group is selected from the group consisting of 2-$^{18}$F-Adenine, 2-$^{18}$F-adenosine, 2-$^{18}$F-AMP, 2-$^{18}$F-ADP, and 2-$^{18}$F-ATP.

5. The method of claim 1, wherein the adenine or adenine containing molecule comprises an $^{11}$C-labeled adenine group or an $^{11}$C-labeled adenosine group.

6. The method of claim 5, wherein the $^{11}$C-labeled adenine group is a 2-$^{11}$C-labeled adenine group or a 2-$^{11}$C-labeled adenosine group.

7. The method of claim 6, wherein the $^{11}$C-labeled adenine group is selected from the group consisting of 2-$^{11}$C-Adenine, 2-$^{11}$C-adenosine, 2-$^{11}$C-AMP, 2-$^{11}$C-ADP, and 2-$^{11}$C-ATP.

8. The method of claim 1, wherein the patient has cystic fibrosis or cancer.

9. A method of localizing and imaging tumors and metastases in a patient using positron emission tomography, wherein the patient has a disease with abnormal adenosine and ATP transport and metabolism, wherein the method comprises administering to the patient radiolabeled oxygenated adenine or a radiolabeled oxygenated adenine containing molecule, wherein the oxygenated adenine or oxygenated adenine containing molecule is radiolabeled on the adenine group with $^{11}$C, $^{18}$F or $^{13}$NH$_2$, and tracing biodistribution of the radiolabeled oxygenated adenine or radiolabeled oxygenated adenine containing molecule by positron emission tomography for imaging and localizing the tumors and metastases.

10. The method of claim 9, wherein the adenine or adenine containing molecule comprises an $^{18}$F-labeled adenine group.

11. The method of claim 10, wherein the adenine or adenine containing molecule comprises a 2-$^{18}$F-labeled adenine group.

12. The method of claim 11, wherein the $^{18}$F-labeled adenine group is selected from the group consisting of 2-$^{18}$F-Adenine, 2-$^{18}$F-adenosine, 2-$^{18}$F-AMP, 2-$^{18}$F-ADP, and 2-$^{18}$F-ATP.

13. The method of claim 9, wherein the adenine or adenine containing molecule comprises an $^{11}$C-labeled adenine group or an $^{11}$C-labeled adenosine group.

14. The method of claim 13, wherein the $^{11}$C-labeled adenine group is a 2-$^{11}$C-labeled adenine group or a 2-$^{11}$C-labeled adenosine group.

15. The method of claim 14, wherein the $^{11}$C-labeled adenine group is selected from the group consisting of 2-$^{11}$C-Adenine, 2-$^{11}$C-adenosine, 2-$^{11}$C-AMP, 2-$^{11}$C-ADP, and 2-$^{11}$C-ATP.

16. The method of claim 9, wherein the patient has cancer.

17. The method of claim 9, wherein the tumors are tumor micrometastases.

18. A method of assessing alterations in adenylate metabolism in a patient, wherein the patient has a disease with abnormal adenosine and ATP transport and metabolism, wherein the method comprises administering to the patient a $^{11}$C radiolabeled oxygenated adenine or a $^{11}$C radiolabeled oxygenated adenine containing molecule, wherein said $^{11}$C radiolabeled oxygenated adenine or $^{11}$C radiolabeled oxygenated adenine containing molecule is radiolabeled with $^{11}$C on the adenine group, and tracing biodistribution of said $^{11}$C radiolabeled oxygenated adenine or $^{11}$C radiolabeled oxygenated adenine containing molecule by positron emission tomography for assessing alterations in adenylate metabolism in the patient.

* * * * *